United States Patent [19]
Horiuchi et al.

[11] Patent Number: 5,406,368
[45] Date of Patent: Apr. 11, 1995

[54] METHOD AND APPARATUS FOR CHROMATIC DISPERSION MEASUREMENTS

[75] Inventors: Yukio Horiuchi, Niza; Yoshinori Namihira, Hachioji; Hiroharu Wakabayashi, Kawasaki, all of Japan

[73] Assignee: Kokusai Denshin Denwa Kabushiki Kaisha, Tokyo, Japan

[21] Appl. No.: 175,924

[22] Filed: Dec. 30, 1993

[30] Foreign Application Priority Data

Jul. 6, 1993 [JP] Japan ................... 5-191655

[51] Int. Cl.⁶ ............................................ G01N 21/84
[52] U.S. Cl. .................................................. 356/73.1
[58] Field of Search ........................................ 356/73.1

[56] References Cited

U.S. PATENT DOCUMENTS 4,984,884 1/1991 Ryu et al. ........................... 356/73.1

OTHER PUBLICATIONS

Horiuchi et al "Chromatic Dispersion Measurements of 4564 Km Optical Amplifier Repeater System"; Electronics Letters; 7 Jan. 1993; vol. 29 No. I; pp. 4–5.

*Primary Examiner*—Vincent P. McGraw
*Attorney, Agent, or Firm*—Emmanuel J. Lobato

[57] ABSTRACT

A chromatic dispersion measuring method and apparatus are disclosed which permit highly accurate measurements of the wavelength dispersion characteristic of an optical transmission such as an optical fiber or an optical amplifier repeater system. Measurements are made on the propagation time of a first optical signal of a fixed wavelength through an optical transmission line to be measured and the propagation time through the same optical transmission line of a second optical signal whose wavelength can be arbitrarily set over the measuring wavelength band. By obtaining a difference between the both propagation times, it is possible to obtain only a change in the propagation time of each signal which is caused by a change in the wavelength of the second optical signal. That is, the elongation or shrinkage of the optical fiber has an equal influence on both of the first optical signal and the second optical signal, and hence does not induce an error in the detection of the above-said time difference.

3 Claims, 8 Drawing Sheets

METHOD AND APPARATUS FOR CHROMATIC DISPERSION MEASUREMENTS

BACKGROUND OF THE INVENTION

The present invention relates to chromatic dispersion measuring method and apparatus for measuring the chromatic dispersion characteristic of optical signals which are transmitted over optical transmission lines such as an optical fiber and an optical amplifier repeater system having multiple stages of optical fibers connected via optical amplifiers.

The chromatic dispersion characteristic of an optical fiber is obtainable from the degradation of the propagation time relative to the wavelength of an optical signal, that is, from the group delay characteristic, and it is usually expressed by the propagation time difference per unit wavelength.

In a fiber optic communication using an optical fiber as a transmission line, the waveform of the optical signal after transmission is distorted owing to the relationship between spreading of the wavelength of the optical signal and the chromatic dispersion characteristic of the optical fiber, so that this leads to degradation of the receiving characteristic. Moreover, in an optical amplifier repeater system, the chromatic dispersion characteristic of optical fibers forming the system is accumulated, and hence a non-linear effects of the optical fibers by such a chromatic dispersion characteristic seriously affect the transmission characteristic. It is essential, therefore, for the construction of an optical communication system to study the chromatic dispersion characteristic in detail.

Figure 9:
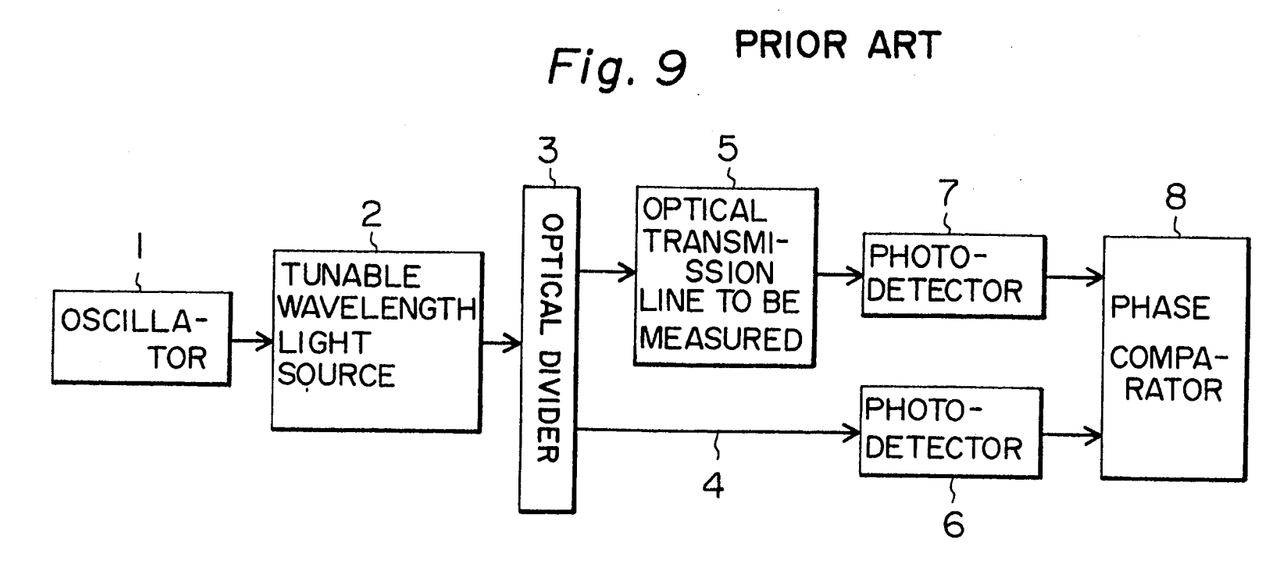
FIG. 9 is a block diagram explanatory of a conventional chromatic dispersion measuring method.

FIG. 9 is a block diagram showing a first conventional light chromatic dispersion measuring apparatus.

In FIG. 9, reference numeral 1 denotes an oscillator for generating a single-frequency signal, 2 a tunable-wavelength light source formed by a plurality of light sources of different wavelengths or a tunable-wavelength light source formed by a single light source but capable of oscillating at a plurality of wavelengths, 3 an optical divider for splitting the output from the tunable-wavelength light source 2, 4 a reference optical fiber, 5 an optical transmission line to be measured, such as an optical fiber or optical amplifier repeater system having one or more stages of optical fibers connected via optical amplifiers, 6 a light receiver or photodetector for converting the optical signal output from the reference optical fiber 4 to an electrical signal, 7 an optical receiver or photodetector for converting the optical signal output from the optical transmission line 5 to an electrical signal, and 8 a phase comparator for mutually comparing the phases of the electrical signals output from the photodetectors 6 and 7.

The oscillator 1 supplies to the tunable-wavelength light source 2 a single-frequency signal which is used for intensity modulation of the optical signal output therefrom. The intensity-modulated optical signal from the tunable-wavelength light source 2 is split by the optical divider 3. The one of such split optical signals is used as a reference for phase comparison; it is provided to a reference input of the phase comparator 8 via the reference optical fiber 4 of a short length and the photodetector 6. The other optical signal is input into the phase comparator 8 via the optical transmission line 5 and the photodetector 7. The phase comparator 8 detects a phase difference between two input optical signals. By performing this for each wavelength, the group delay characteristic can be obtained.

That is, the relative propagation time $\tau(\lambda)$ of light of a wavelength $\lambda$ in the optical transmission line 5 is obtain-able from the measured phase difference $\theta(\lambda)$ as follows:

$$\tau(\lambda) = \theta(\lambda)/360 f$$

where f is the oscillation frequency of the oscillator 1. By converting them to unit distance (km) and representing the abscissa with the wavelength $\lambda$ and the ordinate with $\tau(\lambda)$, the group delay characteristic can be obtained, and by differentiating this $\tau(\lambda)$ with the wavelength $\lambda$, the chromatic dispersion characteristic can be obtained.

The chromatic dispersion measuring apparatus of Prior Art Example 1 involves sequential changing of the wavelength for measurement, and hence needs some amount of measuring time; in this instance, however, an ambient temperature change during a measurement operation causes a change in the length of the optical fiber used as the optical transmission line 5, inducing an error in the measurement of the relative propagation time $\tau(\lambda)$.

There has been proposed a solution to the problem of elongation and shrinkage of the optical fiber by the ambient temperature change (Japanese Pat. Pub. No. 54292/91 entitled "Method for Measuring the Dispersion Characteristic of Optical Fibers"). It will herein below be described as Prior Art Example 2.

Figure 10:
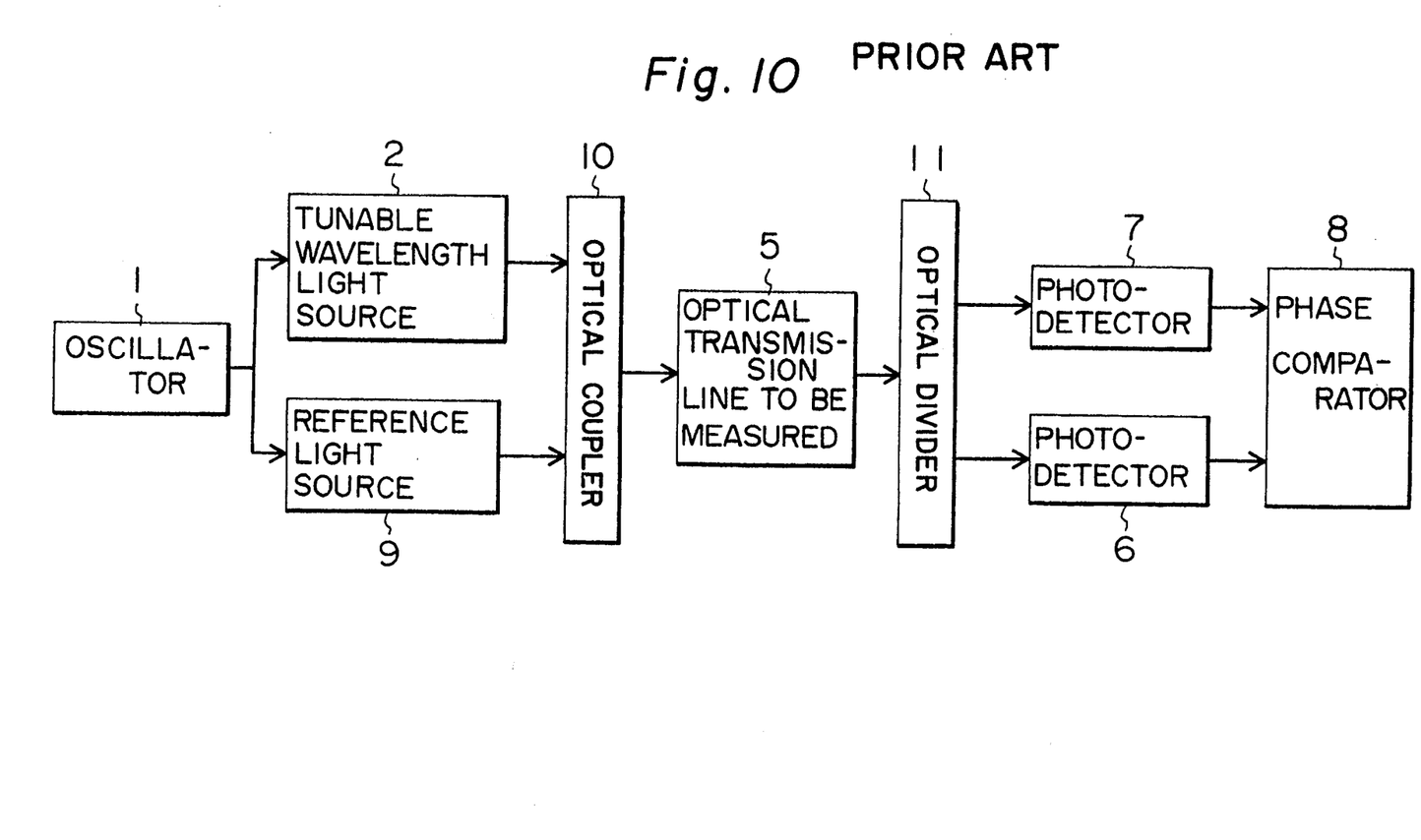
FIG. 10 is a block diagram explanatory of another conventional chromatic dispersion measuring method.

FIG. 10 is a block diagram illustrating a second conventional light chromatic dispersion measuring apparatus.

In this example, the parts corresponding to those in Prior Art Example 1 are identified by the same reference numerals and no description will be given of them. In FIG. 10, reference numeral 9 denotes a reference light source for emitting a reference signal for phase comparison use which has an optical signal wavelength different in region from the optical signal wavelength of the tunable-wavelength light source 2, 10 an optical coupler for coupling the output light from the tunable-wavelength light source 2 and the output light from the reference light source 9, and 11 a wavelength selection typed light splitter for splitting the optical signals from the tunable-wavelength light source 2 and from the reference light source 9 in their respective wavelength regions.

The oscillator 1 supplies to the tunable-wavelength light source 2 and the reference light source 9 a single-frequency signal for intensity modifying their optical signal outputs. The intensity-modulated optical signals from the tunable-wavelength light source 2 and the reference light source 9 are coupled together by the optical coupler 10. The two optical signals thus coupled are both input into the optical transmission line 5 and propagate therethrough. The optical signals having thus propagated through the optical transmission line 5 are separated by the wavelength selection typed optical divider 11 into the optical signal from the tunable-wavelength light source 2 and the optical signal from the reference light source 9. The thus separated optical signal from the reference light source 9 is provided via the photodetector 6 to a reference input of the phase comparator 8 for use as a signal reference in phase comparison. The optical signal from the tunable-wavelength light source 2 is provided via the photodetector 7 to the phase comparator 8. The phase comparator 8 detects a phase difference between the two optical signals. By performing this for each wavelength, the group delay characteristic can be obtained.

For example, in case of measuring a 1.55 μm chromatic dispersion characteristic of an optical fiber, the oscillation wavelength of the tunable-wavelength light source 2 is set to a 1.55 μm band, whereas the oscillation wavelength of the reference light source 9 is set to an entirely different 1.3 μm band. By setting the wavelength of the reference signal to such a wave-length band different from that of the optical signal from the tunable-wavelength light source 2, the two optical signals can be separated by the wavelength selection typed optical divider 11, and the phase comparison can be made by using the 1.3 μm band optical signal as the reference signal for phase measurement. Since the two optical signals propagate through the same optical fiber, this prior art example is free from the measurement error which results from elongation and shrinkage of the optical fiber.

As described above, according to Prior Art Example, 1, since the reference signal light and the signal light to be measured propagate through different paths, the elongation or shrinkage of the optical fiber for the light to be measured, by an ambient temperature change, seriously affects the time for propagation of the signal light through the optical fiber, impairing the accuracy of measurement of the chromatic dispersion characteristic.

On the other hand, Prior Art Example 2 avoids the influence of elongation and shrinkage of the optical fiber by simultaneously propagating the reference signal light and the signal light to be measured through the same optical fiber for the light to be measured. With this method, however, it is necessary that the optical transmission line has a wavelength bandwidth wide enough for transmitting signal components which are sufficiently spaced apart in wavelength to permit the separation of the two optical signals in terms of wavelength which is the feature of the above-mentioned prior art example. Hence, measurement for a single optical fiber can be made, but in an optical amplifier repeater system which has one or more stages of optical fibers connected using light amplifiers of limited transmission wavelength bandwidth, it is very difficult to transmit the reference signal light and the signal light to be measured and separate them at the receiving end, because the light wavelength bandwidth available for transmission is limited. For instance, in a case of a distance corresponding to an optical amplifier repeater system intended for transpacific communication, the optical wavelength available for transmission is as narrow as 2 to 3 nanometers; therefore, it is extremely hard to put the method of Prior Art Example 2 to practical use.

Furthermore, in such an optical amplifier repeater system, the chromatic dispersion characteristics of respective optical fibers forming the system are accumulated; hence, to keep its overall transmission characteristic excellent, it is necessary to measure the chromatic dispersion characteristic of each optical fiber with high precision and perform feedback processing such as equalization of the chromatic dispersion characteristic of the optical repeating system on the basis of the results of measurement.

However, there have not been proposed yet a method and apparatus for measuring the chromatic dispersion characteristic of an optical transmission line which sufficiently satisfy such requirements as mentioned above.

SUMMARY OF THE INVENTION

It is therefore an object of the present invention to provide a method and an apparatus for chromatic dispersion measurement which are free from the above-noted problems of the prior art and hence permit highly accurate measurement of the chromatic dispersion characteristic of an optical transmission line such as an optical fiber or optical amplifier repeater system.

To solve the problems of the prior art referred to above, the chromatic dispersion measuring method according to the present invention is a method in which an optical signal, obtained by modulating the optical output from a light source with a single-frequency signal, is applied to the input end of an optical transmission line such as an optical fiber, the modulated optical signal is received at the output end of the optical transmission line, the wavelength of the optical output is changed and a phase difference between it and the single-frequency signal at the input end is measured, whereby the chromatic dispersion characteristic of the optical transmission line is measured, the chromatic dispersion measuring method comprising:

a step of deriving said optical output from a fixed wavelength first optical signal and a tunable wavelength second optical signal and measuring a change in the light propagation time of said fixed wavelength optical signal through said optical transmission line by its elongation or shrinkage upon each measurement of a change in the light propagation time of said tunable wavelength second optical signal through said optical transmission line;

a step of recording the times of measuring the changes in said light propagation times of said tunable wavelength second optical signal and said fixed wavelength optical signal, respectively;

a step of accurately obtaining, by interpolation, the amount of change in said light propagation time of said second optical signal caused by the elongation or shrinkage of said optical transmission line at said measuring time of said second optical signal, from said measuring time of said first optical signal and the amount of change in said propagation time of said first optical signal; and a step of removing said amount of change in said propagation time by the elongation or shrinkage of said optical transmission line from said amount of change in said propagation time of said second optical signal, thereby eliminating a measurement error resulting from the elongation or shrinkage of said optical transmission line.

The chromatic dispersion measuring apparatus according to the present invention comprises:

an oscillator for generating a single-frequency signal;

light source means for emitting an optical signal composed of a first optical signal and a second optical signal which are emitted alternately with each other, the wavelength of the first optical signal being fixed but the wavelength of the second optical signal being arbitrarily selectable over the measuring wavelength band and being changed by a desired value each time it is emitted;

a modulator for intensity-modulating the optical signal from the light source means by the signal-frequency signal from the oscillator;

an optical transmission line for propagating therethrough the intensity-modulated optical signal;

phase comparator means for detecting a phase difference between the optical signal propagated through the optical transmission line and the single-frequency signal from the oscillator; and a chromatic dispersion calculator which obtains the phase difference from the phase comparator means and, each time the first optical signal and the second optical signal are emitted from the light source means, measures the propagation times of the first optical signal and the second optical signal through the optical transmission line and records the times of measurement, calculates the difference between the propagation times of the first optical signal and the second optical signal through the optical transmission line and calculates the chromatic dispersion characteristic of the optical transmission line from the calculated time difference.

Measurements are made on the propagation time of a first fixed wavelength optical signal through an optical transmission line and the propagation time therethrough of a second optical signal whose wavelength are arbitrarily selected over the measuring wavelength band, and then a difference between the light propagation times is calculated, by which it is possible to obtain only a change in the propagation time resulting from a wavelength change. In other words, the elongation or shrinkage of the optical fiber has an equal influence on the propagation of the first optical signal and the second optical signal through the optical transmission line, and hence does not form the cause of an error in the calculation of the above-said time difference.

BRIEF DESCRIPTION OF THE DRAWINGS

The present invention will be described in detail below with reference to the accompanying drawings, in which.

PREFERRED EMBODIMENTS OF THE INVENTION

Figure 1:
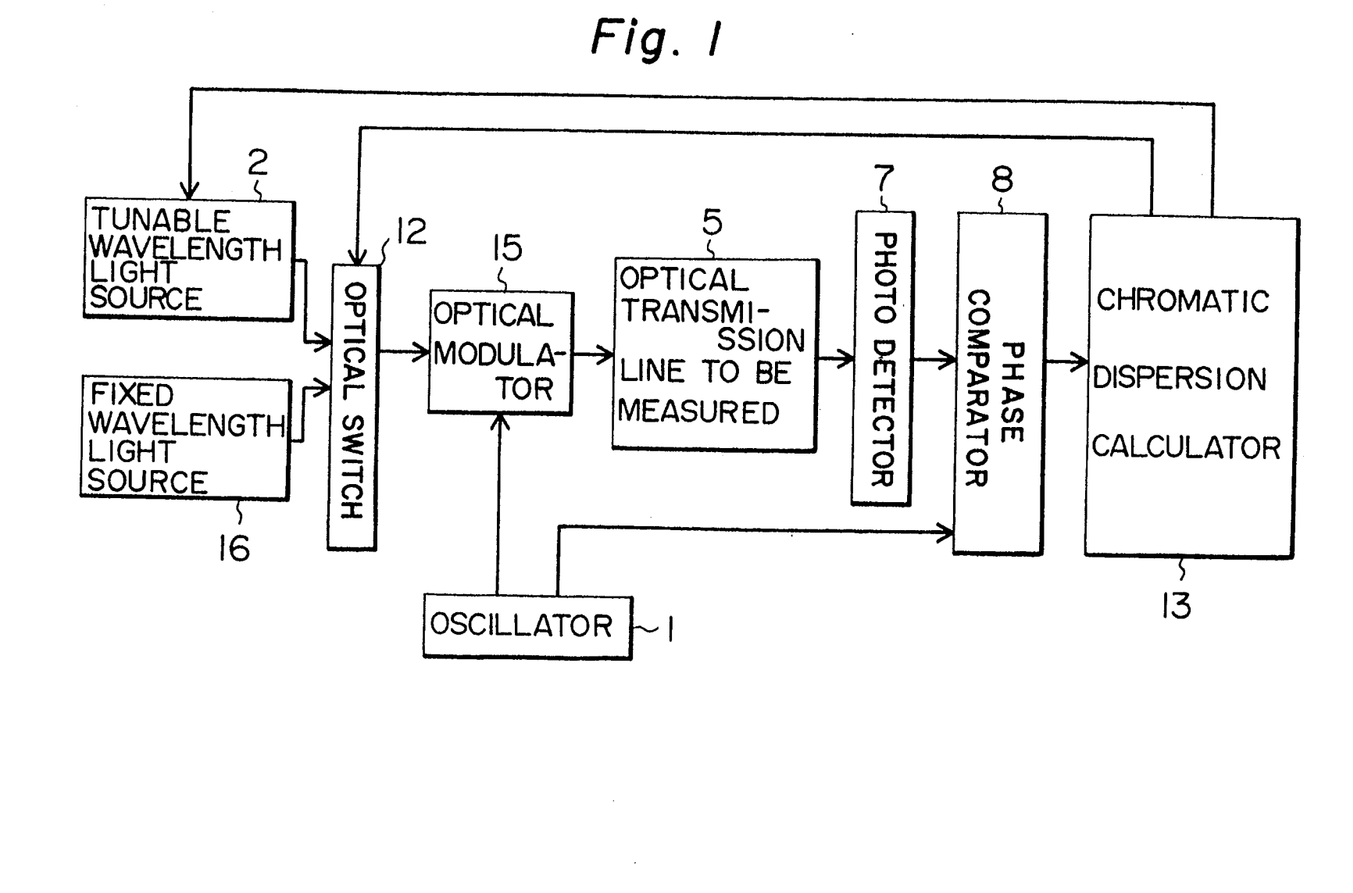
FIG. 1 is a block diagram illustrating a first embodiment of the present invention.

With reference to FIG. 1 illustrating in block form a first embodiment of the chromatic dispersion measuring apparatus according to the present invention, reference numeral 2 denotes a tunable wavelength light source which permits the emission of light from a single light source at a plurality of wavelengths through temperature control, which light source may also be formed by a combination of a plurality of light sources of difference wavelengths or by a light source of an external resonator structure; 16 denotes a fixed wavelength light source which emits light at one of the wavelengths of the tunable wavelength light source 2; 12 denotes an optical switch for selecting either one of the optical signals from the fixed wavelength light source 16 and the tunable wavelength light source 2; 1 denotes an oscillator which supplies a single-frequency signal; 15 denotes an optical modulator for intensity-modulating the output optical signal from the optical switch 12 in accordance with the single-frequency signal from the oscillator 1; 5 denotes an optical transmission line to be measured, such as an optical fiber or optical amplifier repeater system which has one or more stages of optical fibers connected using optical amplifiers; 7 denotes a photodetector for converting the optical signal from the optical transmission line 5 to an electrical signal; 8 denotes a phase comparator for detecting a phase difference between the electrical signals from the photodetector 7 and the oscillator 1; and 13 a chromatic dispersion calculator which controls the switching of the wavelength of the output light from the tunable wavelength light source 2 and the switching operation of the optical switch 12, obtains the phase difference from the phase comparator 8, measures the relative propagation time of the optical signal propagating through the optical transmission line 5 and records the time of measurement and calculates the group delay characteristic and the chromatic dispersion characteristic of the optical transmission line 5. In this embodiment an ordinary personal computer is used as the chromatic dispersion calculator 13.

Figure 2:
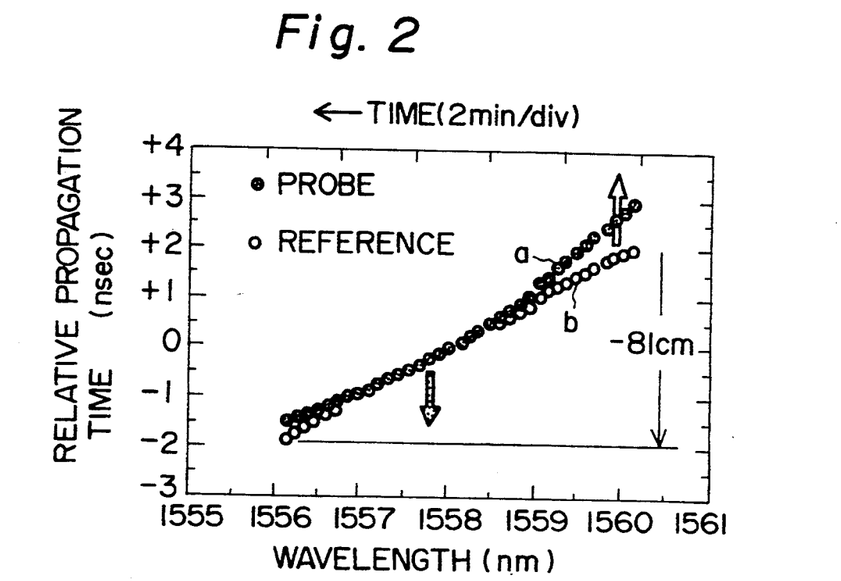
FIG. 2 is a characteristic diagram explanatory of the results of measurements by the first embodiment of the invention.

The tunable wavelength light source 2 was caused to emit optical signals of 36 wavelengths at intervals of 0.1 nm or so over a wavelength band ranging from 1556 to 1560 nm. The fixed wavelength light source 16 was caused to emit a reference optical signal of a 1558 nm wavelength. The optical switch 12 is controlled by the chromatic dispersion calculator 13 to output the optical signal from the tunable wavelength light source 2 and the optical signal from the fixed wavelength light source 16 alternately with each other, and upon each switching of the optical switch 12, the wavelength of the optical signal from the tunable wavelength light source 2 is changed by a predetermined value. The oscillator 1 applies a 1.2 GHz frequency signal to the optical modulator 15 which is a LiNbO$_3$ intensity modulator and the phase comparator 8. Consequently, the reference signal light of the 1558 nm wavelength and the signal light to be measured whose wavelength ranges from 1556 to 150 nm alternately pass through the optical transmission line 5. The optical transmission line 5 was formed by a 4564 km long optical amplifier repeater system composed of 138 optical amplifiers and a 138-cascaded, 33 km long optical fiber. The reference signal light and the signal light to be measured, which have passed through the optical transmission line 5, are received by the photodetector 7, and the output electrical signal from the photodetector 7 and the single-frequency signal from the oscillator 1 are compared in phase with each other by the phase comparator 8, by which the relative propagation time is measured. The chromatic dispersion calculator 13 records the time of measurement for the signal of each wavelength. FIG. 2 shows the results of measurements of the relative propagation time for respective signal light of the wavelengths ranging from 1556 to 1560 nm.

Moreover, on the basis of the relative propagation time of the signal light to be measured and the relative propagation time of the reference signal light measured in proximity to the time of measurement for the signal light to be measured, the chromatic dispersion calculator 13 calculates the elongation or shrinkage of the optical transmission line 5 at the time of measurement for the signal light to be measured. Then the calculator 13 obtains a relative propagation time difference from which a measurement error by the elongation or shrinkage of the optical transmission line has been removed, calculates therefrom the group delay indicated by the curve a in FIG. 3 and then computes therefrom the chromatic dispersion.

FIG. 2 shows the results of actual measurements concerning the removal of measurement errors which may be induced by the elongation or shrinkage of the optical transmission line 5 in the chromatic dispersion measuring method according to the present invention.

Figure 3:
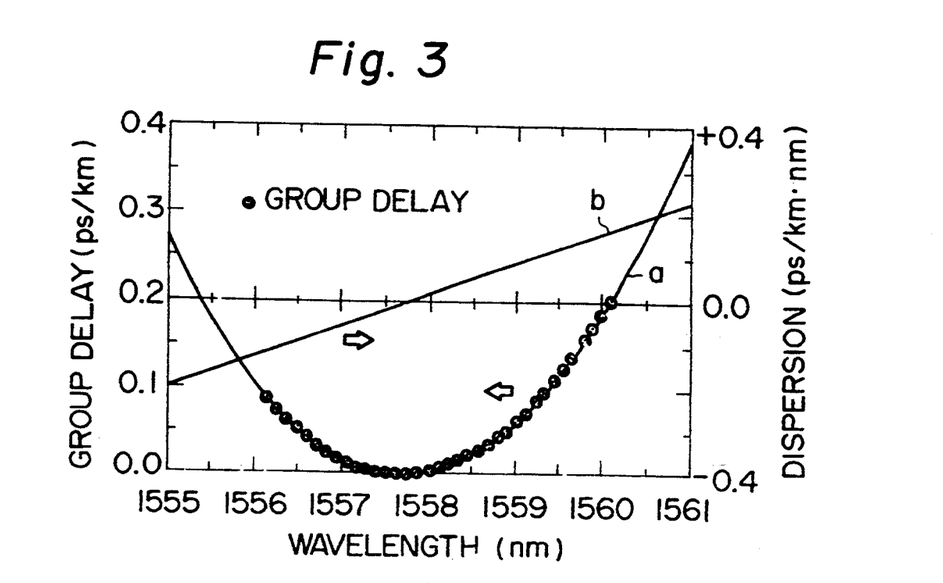
FIG. 3 is a characteristic diagram explanatory of the results of measurements by the first embodiment of the invention.

The characteristic a in FIG. 2 represents the relative propagation time of the signal light from the tunable wavelength light source 2, whereas the characteristic b in FIG. 2 represents the relative propagation time of the reference signal light from the fixed wavelength light source 16 and indicates the influence of the elongation or shrinkage of the optical transmission line 5. It is understood from the characteristic b in FIG. 2 that the length of the optical fiber forming the system decreased as much as 81 cm during measurement. It is the group delay characteristic a in FIG. 3 that is obtained by subtracting b in FIG. 2 from a in FIG. 2. By differentiating the group delay characteristic by waveform, the chromataic dispersion characteristic b in FIG. 3 is obtained.

Figure 4:
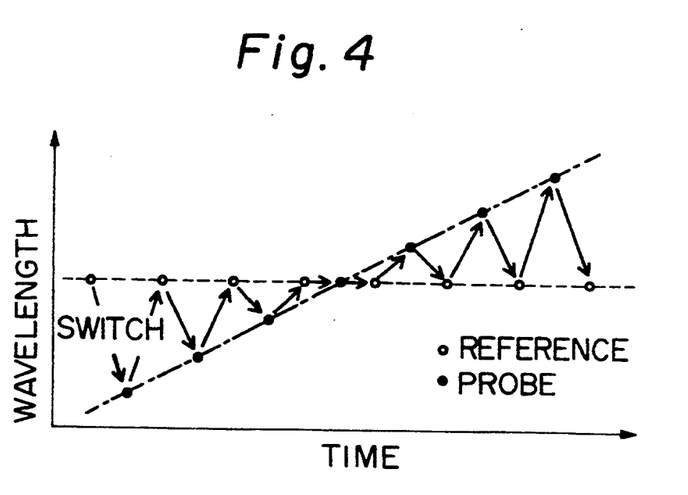
FIG. 4 is a characteristic diagram explanatory of the results of measurements by the first embodiment of the invention.

The process flow of the chromatic dispersion calculator 13 may be summarized as the following steps of:

(1) measuring the relative propagation time ($\tau r(i)$) of the reference signal light from the fixed wavelength light source 16 propagating through the optical transmission line 5 and recording the measuring time (tr(i));

(2) changing the wavelength λ(i) of the signal light to be emitted from the tunable wavelength light source 2 to a target value, measuring the relative propagation time ($\tau p(i)$) of the signal light of the wavelength (λ(i)) propagating through the optical transmission line 5 and recording the measuring time (tp(i));

(3) repeating the steps (1) to (2) by a predetermined number of times (n times) while changing the wavelength (λ(i)) in the step (2) sequentially to predetermined values over the measuring wavelength bandwidth, as shown in FIG. 4; and (4) measuring the relative propagation time ($\tau r(n+1)$) of the reference signal light from the fixed wavelength light source 16 propagating through the optical transmission line 5 and recording the measuring time (tr(n+1)).

Figure 5:
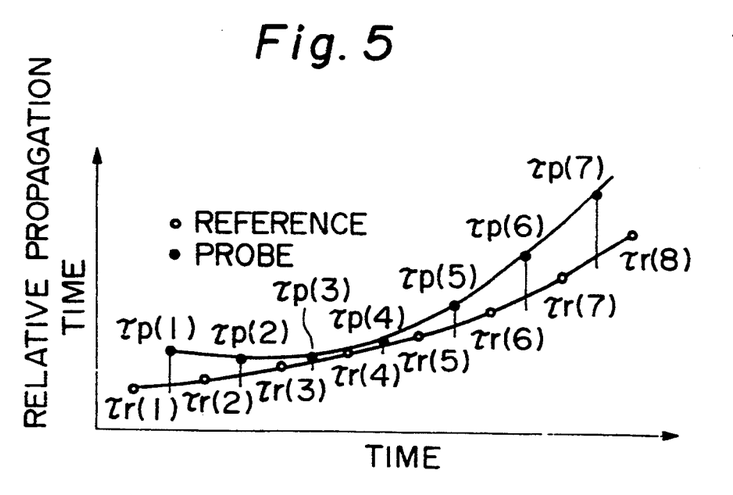
FIG. 5 is a characteristic diagram explanatory of the results of measurements by the first embodiment of the invention.
Figure 6:
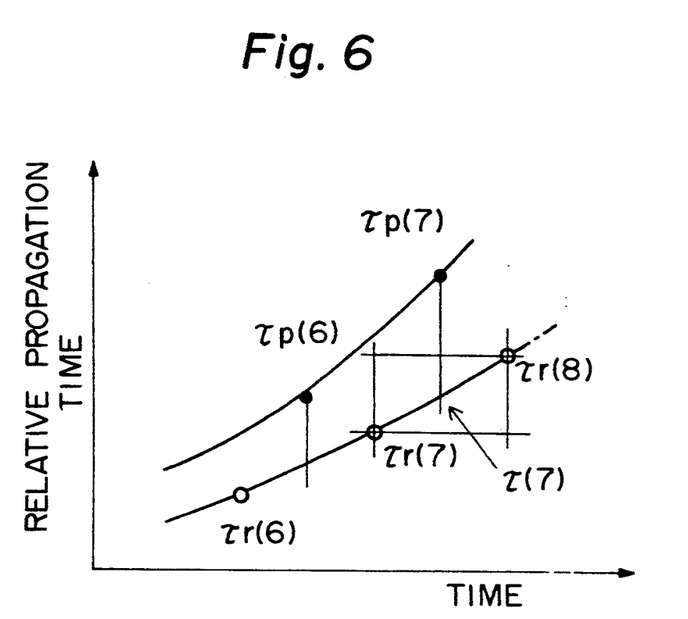
FIG. 6 is a characteristic diagram explanatory of the results of measurements by the first embodiment of the invention.

The relative propagation time ($\tau r(i)$) measured in step (1) for the reference signal light of the fixed wavelength indicates a change in the length of the optical transmission line 5. The relative propagation time ($\tau p(i)$) measured while changing the wavelength (λ(i)) of the signal light from the tunable wavelength light source 2 in step (2) contains a group delay time ($\tau g(i)$) and a delay time ($\tau \tau(i)$) by a change in the length of the optical transmission line 5 ($\tau p(i) = \tau g(i) + \tau(i)$). Obtaining the delay time ($\tau(i)$), it is possible to obtain the desired group delay time ($\tau g(i)$). Since the optical fiber forming the optical transmission line 5 is low in its thermal response speed and undergoes no rapid change in its length with an ambient temperature change, the delay time ($\tau(i)$) can be computed from the following equation (1) by the use of the linear interpolation method. [See, FIGS. 5 and 6]

$$\tau(i) = r(i) + \frac{\tau r(i+1) - \tau r(i)}{tr(i+1) - tr(i)} \times (tp(i) - tr(i)) \quad (1)$$

Therefore, the group delay time ($\tau g(i)$) can be computed by the following equation (2).

$$\tau g(i) = \tau p(i) - \tau(i) \quad (2)$$

While this embodiment computes the delay time ($\tau(i)$) by linear interpolation using two-point data tr(i), $\tau r(i)$ and tr(i+1), $\tau r(i+1)$, it is also possible to easily calculate the delay time by a known method which collectively interpolates measuring points by the use of (n+1) pieces of data tr(1), $\tau r(1)$ through tr(n+1), $\tau r(n+1)$. Incidentally, the group delay time ($\tau g(i)$) can be computed by the following equation (3) using the relative propagation time ($\tau r(i)$) measured in proximity to the relative propagation time ($\tau r(i)$).

$$\tau g(i) = \tau p(i) - \tau r(i) \quad (3)$$

In general, the group delay characteristic obtained through measurement is approximated by an approximate expression. For instance, according to the recommendation given in ITU (formerly known as CCITT) "Report of WP5/XV SGXV. TD-142, 143, 1989, " it is shown that a least square quadratic expression is effective as the approximation expression of the group delay characteristic in the wavelength band ranging from 1.5 to 1.6 μm. This approximation expression is given below.

$$\tau gd(\lambda) = A\lambda^2 + B\lambda + C \quad (4)$$

where A, B and C are constants.

Hence, by differentiating the above-mentioned value $\tau gd(\lambda)$ with the wavelength A after obtaining the above approximation equation by the use of a measured value $\tau g(\lambda)$, the wavelength dispersion D(A) can be obtained by the following equation.

$$D(\lambda) = 2A\lambda + B \quad (5)$$

Figure 7:
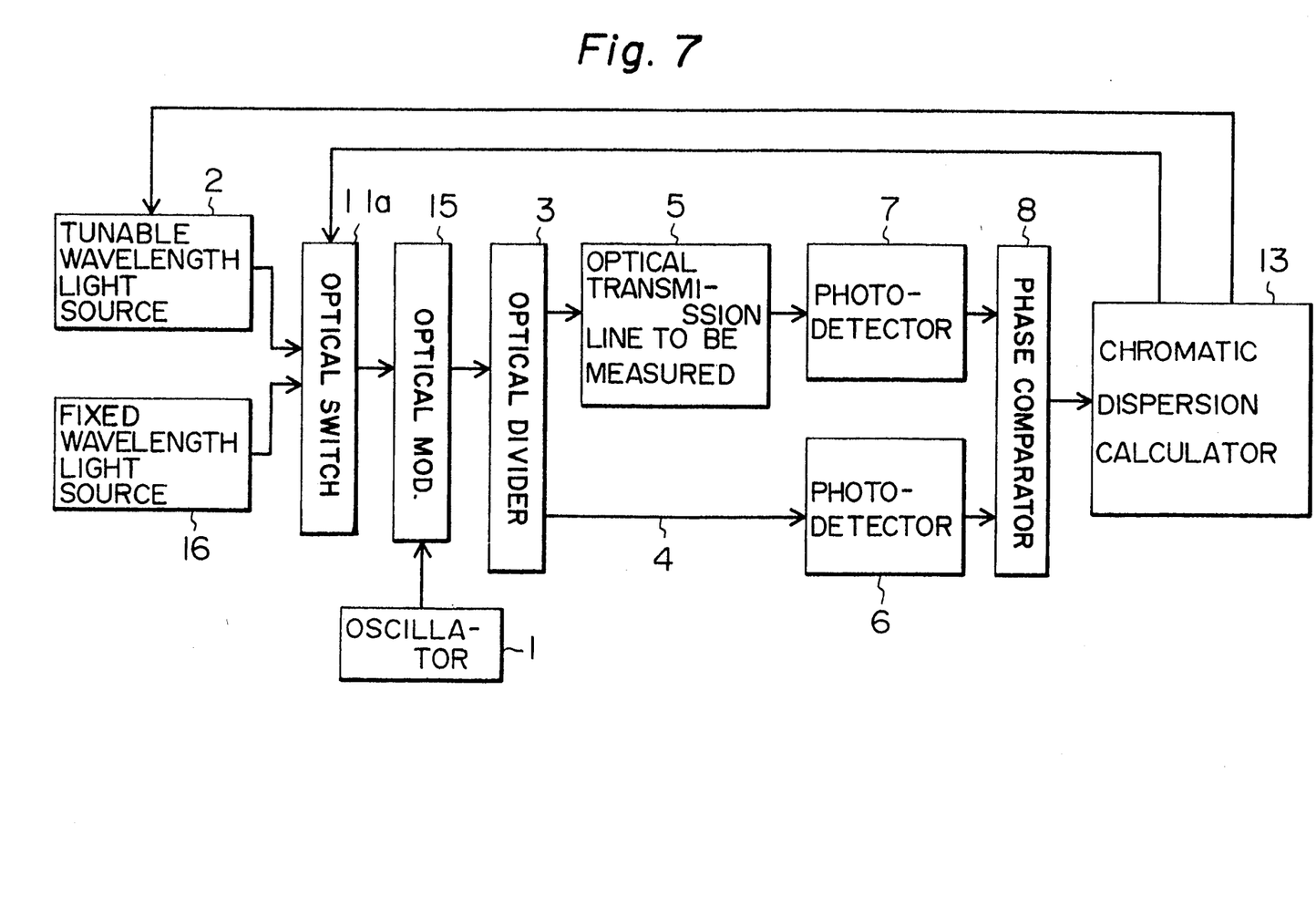
FIG. 7 is a block diagram illustrating a second embodiment of the present invention.

FIG. 7 illustrates in block form the chromatic dispersion measuring apparatus according to a second embodiment of the present invention.

The parts corresponding to those in Embodiment 1 are identified by the same reference numerals. In FIG. 7, reference numeral 3 denotes an optical divider for splitting the output light from the optical modulator 15, 4 a reference optical fiber, and 6 a photodetector for converting the output from the reference optical fiber to an electrical signal.

Embodiment 2 differs from Embodiment 1 in that the signals for phase comparison are obtained from the signal light from the tunable wavelength light source 2 and the reference signal light from the fixed wavelength light source 16.

That is, the output light from the optical modulator 15 is split by the optical divider 3, the split optical signal is propagated through the reference optical fiber 4 and the optical signal thus propagated therethrough is converted by the photodetector 6 to an electrical signal, which is input into the phase comparator 8.

In Embodiment 1, when the optical signal for propagation through the optical transmission line 5 is modulated by the optical modulator 15, the signal phase of the modulated signal output may sometimes be changed by the wavelength characteristic of the optical modulator 15. On the other hand, since the reference signal which is applied to the phase comparator 8 is provided thereto directly from the oscillator 1, there is a case where an error is induced which includes the wavelength characteristic of the optical modulator 15 in the measured results. In Embodiment 2, however, since the reference signal to the phase comparator 8 is the output from the optical modulator 15, it is cancelled by the wavelength characteristic of the optical modulator 15, precluding the possibility of the above-said error being induced.

Figure 8:
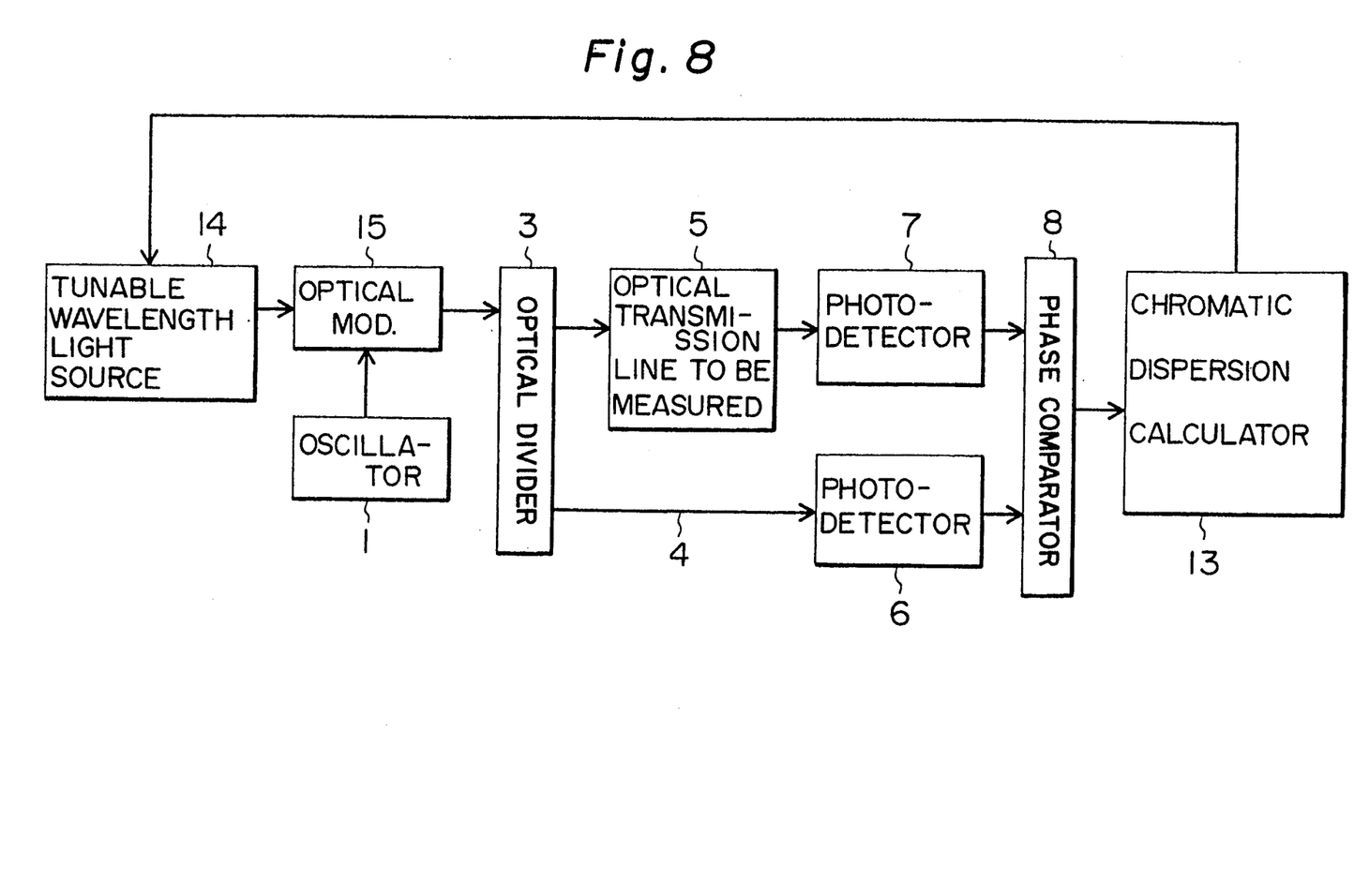
FIG. 8 is a block diagram illustrating a third embodiment of the present invention.

FIG. 8 illustrates in block form the chromatic dispersion measuring apparatus according to a third embodiment of the present invention.

No description will be given of the same parts as those in Embodiment 2. In FIG. 8, reference numeral 14 denotes a tunable wavelength light source of an external resonator structure which is extremely high in the wavelength switching speed. While in Embodiment 2 the fixed wavelength light source 9 and the tunable wavelength light source 2 are switched by the optical switch 11a, the tunable wavelength light source 14 of high wavelength switching speed can be used as a substitute for all of the light sources 9 and 2 and the optical switch 11a and produces the same excellent effects as those obtainable with Embodiment 2.

In Embodiments 1, 2 and 3 the optical modulator is used to intensity modulate the optical signal by the single-frequency signal, but in the case of using a light possible of direct modulation, the oscillator output may be applied to the light source for direct modulation.

As described above in detail, the present invention permits sufficient removal of measurement errors resulting from elongation or shrinkage of an optical fiber, and hence enables highly accurate measurements of chromatic dispersions.

Thus, the dispersion measuring method according to the present invention can be widely used as means for measuring the dispersion characteristics of a fiber optic communication system and an optical amplifier repeater system which require strictly grasping their dispersion characteristics and the optical fibers forming such systems; hence, the present invention is of great utility in practical use.

What we claim is:

1. A chromatic dispersion characteristic measuring method wherein an optical signal, obtained by modulating the optical output from a light source with a single-frequency signal, is applied to the input end of an optical transmission line to be measured, said modulated optical signal is received at the output end of said optical transmission line, the wavelength of said optical output is changed, and a phase difference between it and said single-frequency signal at said input end of said optical transmission line is measured to thereby measure the chromatic dispersion characteristic of said optical transmission line, said method comprising:
    a step of deriving said optical output from a fixed wavelength first optical signal and a tunable wavelength second optical signal and measuring a change in the light propagation time of said fixed wavelength optical signal through said optical transmission line by its elongation or shrinkage upon each measurement of a change in the light propagation time of said tunable wavelength second optical signal through said optical transmission line;
    a step of recording the times of measuring the changes in said light propagation times of said tunable wavelength second optical signal and said fixed wavelength optical signal, respectively;
    a step of accurately obtaining, by interpolation, the amount of change in said light propagation time of said second optical signal caused by the elongation or shrinkage of said optical transmission line at said measuring time of said second optical signal, from said measuring time of said first optical signal and the amount of change in said propagation time of said first optical signal; and
    a step of removing said amount of change in said propagation time by the elongation or shrinkage of said optical transmission line from said amount of change in said propagation time of said second optical signal, thereby eliminating a measurement error resulting from the elongation or shrinkage of said optical transmission line.

2. A chromatic dispersion measuring apparatus comprising:
    an oscillator for generating a single-frequency signal;
    light source means for generating an optical signal composed of a first optical signal and a second optical signal which are alternately emitted therefrom, the wavelength of said first optical signal being fixed but the wavelength of said second optical signal being arbitrarily selectable over the measuring wavelength band and changed by a desired value each time it is emitted;
    a modulator for intensity modulating said optical signal from said light source means by said single-frequency signal from said oscillator;
    an optical transmission line to be measured which propagates therethrough said intensity-modulated optical signal;
    phase comparator means for detecting a phase difference between said optical signal having propagated through said optical transmission line and said single-frequency from said oscillator; and
    a chromatic dispersion calculator which obtains the phase difference from said phase comparator means and, each time said first optical signal and said second optical signal are emitted from said light source means, measures the propagation times of said first optical signal and said second optical signal through said optical transmission line and records the times of said measurements, calculates the difference between said propagation times of said first optical signal and said second optical signals and computes the chromatic dispersion characteristic of said optical transmission line from said time difference.

3. A wavelength dispersion measuring apparatus according to claim 2, characterized in that said chromatic dispersion calculator has a construction wherein said propagation time of said first optical signal corresponding to the time when said propagation time of said second optical signal was measured is calculated, by interpolation, from said propagation time of said first optical signal measured at a time close to said measuring time, in case of calculation of said difference between said propagation times of said first optical signal and said second optical signals.

* * * * *